(12) United States Patent
Cottrell et al.

(10) Patent No.: US 9,890,096 B2
(45) Date of Patent: *Feb. 13, 2018

(54) METHODS OF MAKING 2,3,3,3-TETRAFLUORO-2-PROPENE

(75) Inventors: Stephen A. Cottrell, Baton Rouge, LA (US); Yuon Chiu, Denville, NJ (US); Haluk Kopkalli, Staten Island, NY (US); Hsueh Sung Tung, Getzville, NY (US); Kevin D. Uhrich, Alden, NY (US); Peter Scheidle, Morristown, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/313,649

(22) Filed: Dec. 7, 2011

(65) Prior Publication Data

US 2012/0184785 A1   Jul. 19, 2012

Related U.S. Application Data

(60) Provisional application No. 61/434,005, filed on Jan. 19, 2011.

(51) Int. Cl.
C07C 17/25 (2006.01)
C07C 17/38 (2006.01)
(Continued)

(52) U.S. Cl.
CPC ............ *C07C 17/21* (2013.01); *C07C 17/087* (2013.01); *C07C 17/206* (2013.01); *C07C 17/25* (2013.01); *C07C 17/38* (2013.01); *C07C 17/383* (2013.01)

(58) Field of Classification Search
CPC ....... C07C 17/206; C07C 17/20; C07C 17/25; C07C 17/087; C07C 17/389
See application file for complete search history.

(56) References Cited

U.S. PATENT DOCUMENTS 5,271,918 A * 12/1993 Patterson et al. ............. 423/485
8,058,486 B2 * 11/2011 Merkel et al. ................. 570/155
(Continued)

FOREIGN PATENT DOCUMENTS

WO   WO 2007144632 A1 * 12/2007 ........... B01D 53/261
WO        2009125201 A2    10/2009
(Continued)

OTHER PUBLICATIONS

International Search Report & Written Opinion dated Jun. 26, 2012, issued in counterpart International application PCT/US2012/021158.

*Primary Examiner* — Medhanit W Bahta
(74) *Attorney, Agent, or Firm* — Bruce O. Bradford

(57) ABSTRACT

Disclosed is a process for the manufacture of 1234yf from 1,1,2,3-tetrachloropropene, abbreviated herein as "TCP," in three integrated steps:
(a) the R-1 hydrofluorination of TCP to form 1233xf in the vapor phase;
(b) the R-2 hydrofluorination of 1233xf to form 244bb in either the liquid phase or in the liquid phase followed by the vapor phase; and
(c) the R-3 dehydrochlorination of the 244bb in either the liquid or the vapor phase to produce 1234yf;
wherein the vapor phase hydrofluorination of TCP in step (a) is carried out at a higher pressure than the liquid phase hydrofluorination of 1233xf; and
wherein the HCl generated during these steps is scrubbed with water to form an acid solution and the organic components are scrubbed with a caustic solution and then dried before further processing.

6 Claims, 2 Drawing Sheets

(51) Int. Cl.
    *C07C 17/383*    (2006.01)
    *C07C 17/21*    (2006.01)
    *C07C 17/20*    (2006.01)
    *C07C 17/087*    (2006.01)

(56) References Cited

U.S. PATENT DOCUMENTS

| | | | |
|---|---|---|---|
| 8,084,653 B2* | 12/2011 | Tung et al. | 570/123 |
| 2002/0168315 A1* | 11/2002 | Ewing et al. | 423/484 |
| 2007/0197842 A1 | 8/2007 | Mukhopadhyay et al. | |
| 2009/0030247 A1* | 1/2009 | Johnson | C07C 17/04 |
| | | | 570/155 |
| 2009/0240090 A1* | 9/2009 | Merkel et al. | 570/160 |
| 2009/0287026 A1* | 11/2009 | Kopkalli | C07C 17/087 |
| | | | 570/156 |
| 2009/0312585 A1* | 12/2009 | Merkel et al. | 570/167 |
| 2010/0036179 A1* | 2/2010 | Merkel et al. | 570/156 |
| 2010/0145111 A1* | 6/2010 | Sharratt et al. | 570/156 |
| 2011/0105807 A1 | 5/2011 | Kopkalli et al. | |
| 2011/0105809 A1 | 5/2011 | Devic et al. | |
| 2011/0130599 A1 | 6/2011 | Elsheikh et al. | |
| 2011/0155942 A1 | 6/2011 | Pigamo et al. | |

FOREIGN PATENT DOCUMENTS

| | | |
|---|---|---|
| WO | 2009138764 A1 | 11/2009 |
| WO | 2011056441 A2 | 5/2011 |
| WO | 2011087825 A1 | 7/2011 |
| WO | 2011110889 A1 | 9/2011 |

* cited by examiner

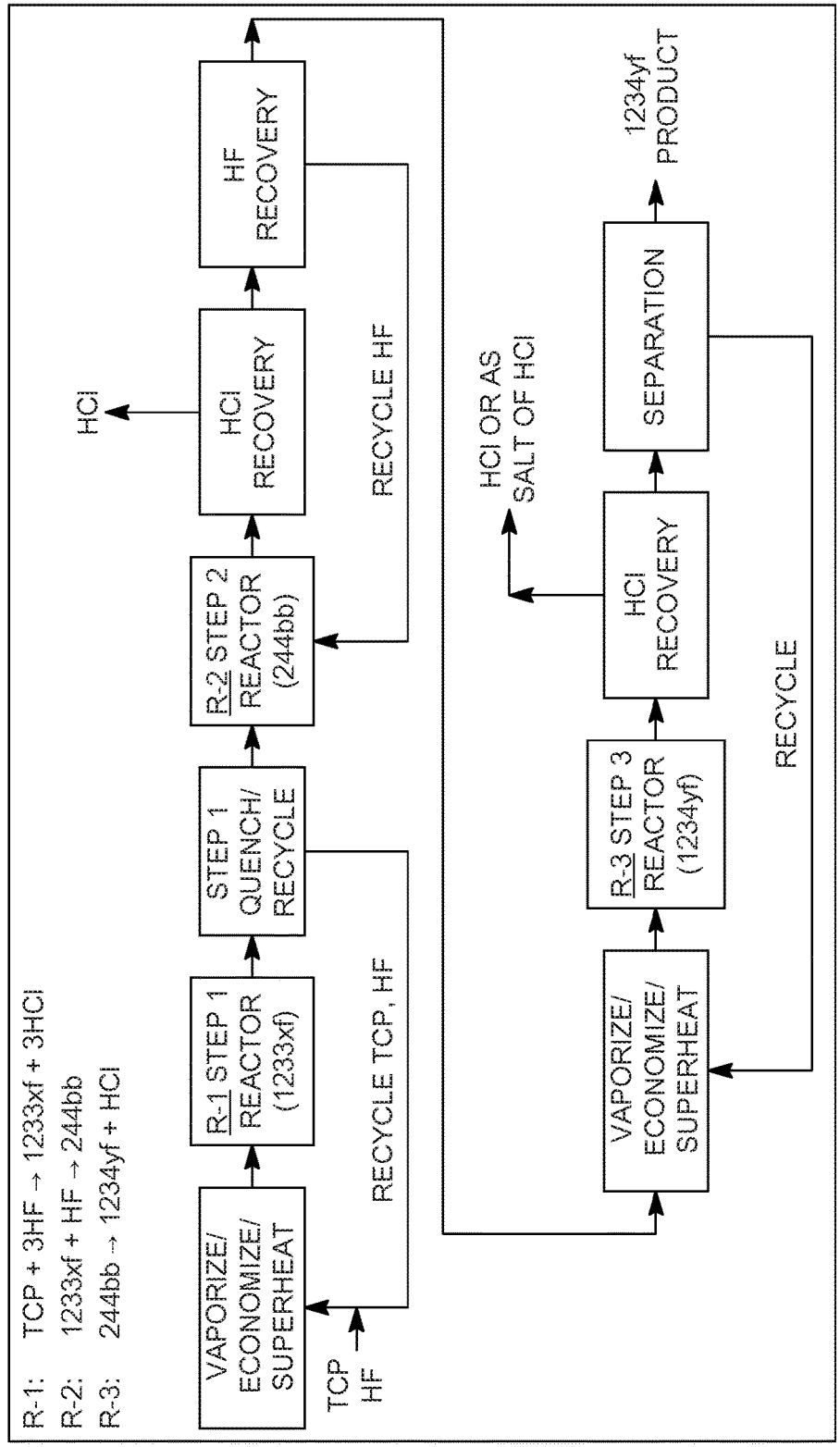
FIG. 1 - SCHEME 1

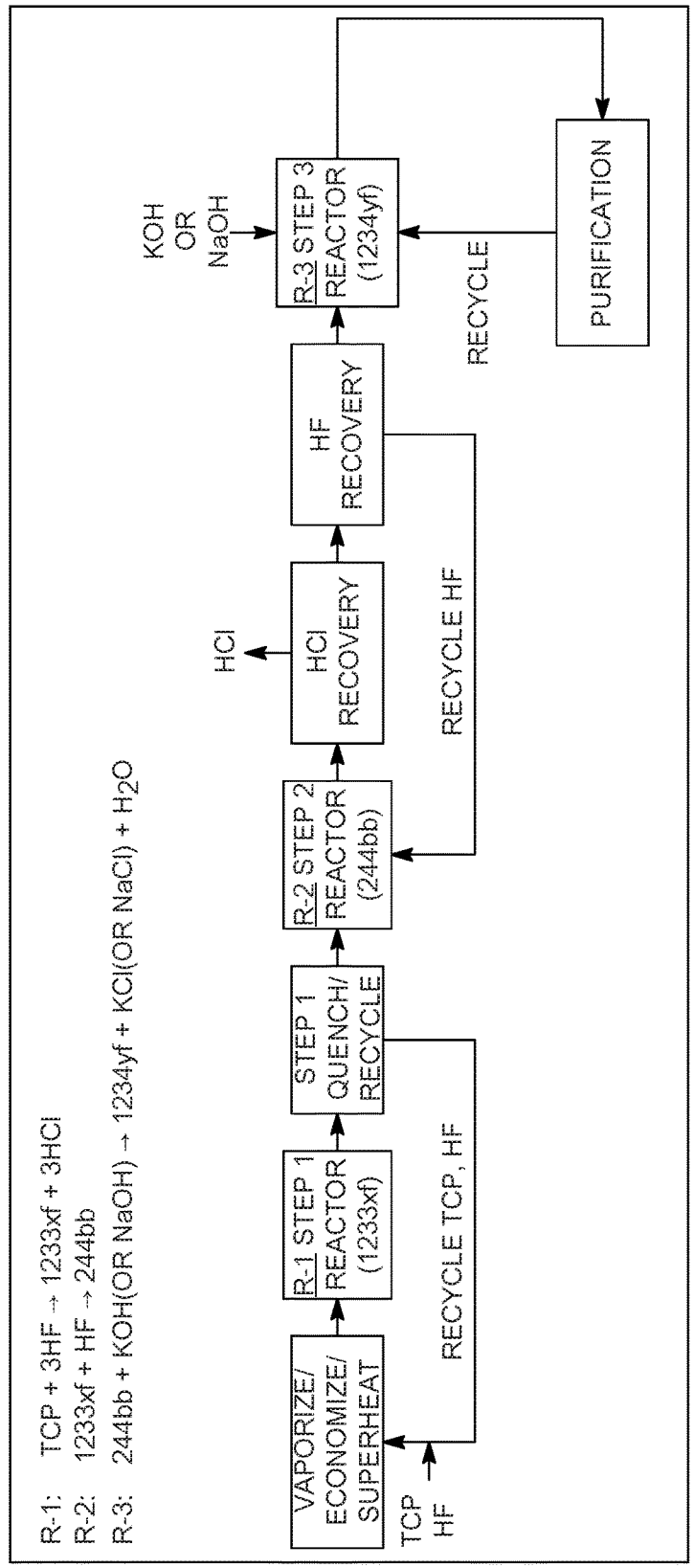
FIG. 2 – SCHEME 2

METHODS OF MAKING 2,3,3,3-TETRAFLUORO-2-PROPENE

CROSS-REFERENCE TO RELATED APPLICATION

This application claims domestic priority from commonly owned, copending, U.S. Provisional Patent Application Ser. No. 61/434,005, filed Jan. 19, 2011, the disclosure of which is hereby incorporated herein by reference.

FIELD OF THE INVENTION

Fluorocarbons, particularly fluorinated olefins, as a class, have many and varied uses, including as chemical intermediates and monomers. In particular, the hydrogenated products are useful as refrigerants, monomers or intermediates for preparing refrigerants, particularly those identified as having low global warming potential.

BACKGROUND OF THE INVENTION

This invention especially relates to improvements in the production of 2,3,3,3-tetrafluoro-2-propene, also known as 1234yf, and having the chemical formula:

$CF_3-CF=CH_2$.

This chemical compound has zero ozone depletion potential and low global-warming potential such that it may be useful and desirable as a replacement for existing materials used in refrigeration, foam blowing and other applications where fluorocarbons such as 1,1,1,2-tetrafluoroethane, also known as 134a, and known also by the chemical formula; $CH_2F-CF_3$, are currently utilized.

WO 2009/138764 discloses a process for the preparation of 1234yf comprising four steps; (1) contacting 1,1,2,3,3,3-hexafluoropropene (1216) with hydrogen in the presence of a hydrogenation catalyst to produce 1,1,2,3,3,3-hexafluoropropane (236ea); (2) dehydrofluorinating 236ea to produce 1,2,3,3,3-pentafluoropropene (1225ye); (3) contacting 1225ye with hydrogen in the presence of a hydrogenation catalyst to produce 1,2,3,3,3-pentafluoropropane (245eb); and (4) dehydrofluorinating (245eb) to produce (1234yf). Part of the process includes the use of $H_2SO_4$ in a drying tower for removal of water from the reactants.

It is known in the art to produce 1234yf from 1,1,2,3-tetrachloropropene (TCP or $CCl_2=CCl-CH_2Cl$) using a non-integrated three step route; see for example US Patent Pub. No. 2007/0197842, the disclosure of which is hereby incorporated herein by reference:

TCP+3HF→1233xf+3HCl (where 1233xf is $CH_2=CCl-CF_3$)

1233xf→244bb (where 244bb is $CF_3-CFCl-CH_3$)

244bb→1234yf+HCl

SUMMARY OF THE INVENTION

This invention provides an integrated process which will decrease the amount of processing equipment required for the process, thereby reducing the capital investment and operating cost, when comparing to a conventional design approach which required separate equipment to produce and isolate each individual process intermediate before subjecting it to further reaction. Hence, this invention provides a much more economical process both from capital and operating standpoints for the production of 2,3,3,3-tetrafluoro-2-propene (1234yf).

One embodiment of this invention is a process for the manufacture of 1234yf from TCP, i.e., 1,1,2,3-tetrachloropropene, in three integrated steps that includes:
 (a) the R-1 hydrofluorination of TCP to form 1233xf in the vapor phase;
 (b) the R-2 hydrofluorination of 1233xf to form 244bb in either the liquid phase or in the liquid phase followed by the vapor phase; and
 (c) the R-3 dehydrochlorination of the 244bb in either the liquid or the vapor phase to produce 1234yf;
 wherein the vapor phase hydrofluorination of TCP in step (a) is carried out at a higher pressure than the liquid phase hydrofluorination of 1233xf; and
 wherein the HCl generated during these steps is scrubbed with water to form an acid solution and the organic components are scrubbed with a caustic solution and then dried before further processing.

As described above, the HCl generated during the process is scrubbed with water to form a solution and the remaining organic components are scrubbed with a caustic solution and dried before being collected. There are several options for drying the organic components:
 (1) passing the stream through a circulating packed tower with sulfuric acid;
 (2) passing the stream through a packed bed of alumina;
 (3) passing the stream through a packed bed of an appropriate molecular sieve, such as 3A;
 (4) passing the stream through a packed bed of silica gel;
 (5) passing the stream through a packed bed of calcium sulfate and/or calcium chloride; and
 (6) combinations of these drying techniques.

As described above, this process advantageously includes steps to remove unwanted HCl formed during the reaction steps by washing with aqueous solutions, followed by drying steps to remove the water from the reaction streams. This washing and drying provides benefits to the overall reaction, including preventing corrosion by eliminating both moisture and acidity that could inhibit the reactions in subsequent processing steps.

Preferably, the hydrofluorination of TCP to 1233xf occurs in the vapor phase in the presence of a fluorination catalyst in a reactor selected from the group consisting of; a single reactor, a multistage reactor, or a series of reactors; using a combination of recycle streams, fresh HF and fresh TCP. The fluorination catalyst is at least one of the following selected from the group consisting of $Cr_2O_3$, Sb/C, $FeCl_3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3, CoCl_2/AlF_3$.

Preferably, the hydrofluorination of 1233xf to 244bb in the liquid phase (or in the liquid phase followed by the vapor phase) and further includes treatment of any reactor effluent containing 1233xf, HCl, excess HF and any unreacted TCP plus intermediates, by feeding this stream into a Quench/Recycle Column for separation of unreacted TCP and excess HF for recycle use in step R-1 of the process.

Preferably, the 1233xf, HCl and HF is fed to a liquid phase reactor containing catalyst selected from $SbCl_3$, $SbCl_5$, $SbF_5$, $TiCl_4$, $SnCl_4$ and combinations thereof for hydrofluorination of 1233xf to 244bb. Preferably, a mixture of 244bb, HCl, unreacted 1233xf and HF exit the liquid reactor system via a catalyst stripper which is used such that most of the unreacted HF and catalyst is refluxed back to the reactor.

Preferably, the effluent from the catalyst stripper may be passed through a bed containing $SbCl_5$/Carbon catalyst for further conversion of 1233xf to 244bb. Advantageously, the effluent from the catalyst stripper or the effluent from $SbCl_5$/C bed is fed to an HCl column to separate essentially pure HCl in the overhead from the mixture of 244bb, 1233xf, HF and HCl.

Advantageously, the mixture of 244bb, 1233xf, HF is fed to an HF Recovery section for recovery and recycle of a stream rich in HF and another stream that is rich in 244bb and 1233xf. One such method is cooling the mixture of 244bb, 1233xf, HF and subjecting to phase separation to separate an organic layer and an HF layer. Another method is the treatment of the mixture of 244bb, 1233xf, HF with a solution of $H_2SO_4$, as disclosed in U.S. Pat. No. 7,371,363, which is hereby incorporated herein by reference.

Preferably, the organic layer which contains minimal amount of HF is fed either directly to a dehydrochlorination reactor or further treated to remove the residual HF. Preferably, the crude 244bb stream is dehydrochlorinated using a vapor phase reactor containing dehydrochlorination catalyst. The catalyst is selected from $Cr_2O_3$, Sb/C, $FeCl_3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$ and combinations thereof. Optionally, the crude 244bb stream is dehydrochlorinated in a liquid phase reactor in the presence of an aqueous base solution. The aqueous base solution is preferably either NaOH or KOH, but other aqueous base solutions may likewise be used herein. See Scheme 2 in the FIGURE.

Preferably, the effluent containing 1234yf, HCl and unreacted 244bb is deacidified in absorption equipment, dried, compressed and fed to a distillation train where 1234yf is recovered and unreacted 244bb recycled to the dehydrochlorination reactor. Advantageously, a portion of any unreacted 244bb is recycled to the liquid phase reactor in order to purge 1233xf. Advantageously, the effluent containing 1234yf, unreacted 244bb and water vapor is dried, compressed and fed to a distillation train where 1234yf is recovered and unreacted 244bb recycled to dehydrochlorination reactor. Preferably, a portion of the unreacted 244bb is recycled to the liquid phase reactor in order to purge 1233xf.

The drying operations that are required during the $3^{rd}$ step of the process may be accomplished using several options:
(1) passing the stream through a circulating packed tower with sulfuric acid;
(2) passing the stream through a packed bed of alumina;
(3) passing the stream through a packed bed of an appropriate molecular sieve, such as 3A;
(4) passing the stream through a packed bed of silica gel;
(5) passing the stream through a packed bed of $CaSO_4$ and/or $CaCl_2$; and
(6) combinations of these drying techniques.

BRIEF DESCRIPTION OF THE DRAWING

FIG. 1 and FIG. 2 show two block flow diagrams (Scheme 1 and Scheme 2, respectively) with processing steps used for the production of 1234yf from TCP, 1,1,2,3-tetrachloropropene.

DETAILED DESCRIPTION OF THE INVENTION

The present invention can be generally described as an integrated process for the production of 1234yf from TCP, 1,1,2,3-tetrachloropropene, in three reaction steps wherein the first reaction is carried out at a higher pressure than the second reaction.

Key features of the integrated process of the present invention include operating the first step vapor phase fluorination reactor at a pressure sufficiently high such that no compression or isolation of intermediates is required for the subsequent liquid phase fluorination reactor. Also, the HCl gas generated in the first step is fed directly to the second step—both to promote mixing and to suppress over-fluorination in the second liquid phase fluorination reactor. The two fluorination reactors are operated with a large excess HF, typically on the order of 20 mol HF to 1 mol organic which, in the first step enhances the vaporization of TCP, and minimizes by-product formation and in the second step, minimizes byproduct formation. The term "integrated process" describes how the process steps are coordinated such that no isolation of intermediate reactants is required. This provides a better yield than non-integrated processes, and reduces the operational costs of the process.

Scheme 1 in the FIGURE describes a process for the manufacture of 1234yf from TCP, 1,1,2,3-tetrachloro-propene, in three integrated steps that include:
(a) the R-1 hydrofluorination of TCP to form 1233xf in the vapor phase;
(b) the R-2 hydrofluorination of 1233xf to form 244bb in the liquid phase (or in the liquid phase followed by the vapor phase); and
(c) the R-3 dehydrochlorination of 244bb in either the liquid or the vapor phase to produce 1234yf.

Preferably, in the Scheme 1 process, the vapor phase hydrofluorination is carried out at a higher pressure than the liquid phase hydrofluorination. Advantageously, in the Scheme 1 process, the TCP, HF and recycle is fed to a vapor phase reactor containing catalyst selected from the group consisting of $Cr_2O_3$, Sb/C, $FeCl_3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$, or a mixture of such catalysts. The reactor used for the hydrofluorination of TCP to 1233xf in the vapor phase is a reactor selected from the group consisting of; a single reactor, a multistage reactor, or a series of reactors; using a combination of recycle streams, fresh HF and fresh TCP.

As illustrated, the hydrofluorination of 1233xf to 244bb in the liquid phase further includes treatment of any reactor effluent containing 1233xf, HCl, excess HF and any unreacted TCP plus intermediates, by feeding this stream into a Quench/Recycle Column for separation of unreacted TCP and excess HF for recycle use in step (R-1) of the process. The 1233xf, HCl and HF is fed to a liquid phase reactor containing catalyst selected from $SbCl_3$, $SbCl_5$, $SbF_5$, $TiCl_4$, and SnCl4 for hydrofluorination of 1233xf to 1,1,1,2-tetrafluoro-2-chloropropane (244bb). The hydrofluorination of 1233xf to 244bb in the liquid phase further includes treatment of any reactor effluent containing 1233xf and 244bb, by feeding this stream into a Quench/Recycle Column for separation of 1233xf for recycle use in step (R-2) of the process.

As illustrated, a mixture of 244bb, HCl, unreacted 1233xf and HF exit the liquid reactor system via a catalyst stripper which is used such that most of the unreacted HF and catalyst is refluxed back to the reactor. The effluent from the catalyst stripper may be passed through a bed containing catalyst for further conversion of 1233xf to 244bb. One preferred catalyst for this conversion is $SbCl_5$ supported on carbon. Preferably, the effluent from the catalyst stripper or the effluent from bed containing $SbCl_5$ supported on carbon is fed to an HCl column to separate essentially pure HCl in the overhead from the mixture of 244bb, 1233xf, HF and HCl.

The essentially pure HCl product is either recovered as is or passed through silica gel for residual HF removal and absorbed into water. HF is recovered from a mixture of 244bb, 1233xf, and HF. One method for HF recovery is by cooling and phase separation to separate a layer rich in organics and a layer rich in HF. This method further includes HF recovery by phase separation and azeotropic distillation. Yet another method for the HF recovery is via absorption into sulfuric acid. Each of these options for HF recovery may be used, alone or in conjunction with the other.

In the process of the present invention, the organic layer which contains minimal amount of HF is fed either directly to a dehydrochlorination reactor or is deacidified. When the crude 244bb stream is dehydrochlorinated, a vapor phase reactor containing a dehydrochlorination catalyst selected from $Cr_2O_3$, Sb/C, and $FeCl3$, $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$ and combinations thereof is employed.

As illustrated in Scheme 2 of the FIGURE, when the crude 244bb stream is dehydrochlorinated in a liquid phase reactor, an aqueous base solution is employed. The aqueous base solution is preferably either NaOH or KOH. When the effluent containing 1234yf, HCl and unreacted 244bb is deacidified in absorption equipment, dried, compressed and fed to a distillation train, 1234yf is recovered and unreacted 244bb is recycled to the dehydrochlorination reactor. Preferably, a portion of any unreacted 244bb is recycled to the liquid phase reactor in order to purge 1233xf. When the effluent containing 1234yf, unreacted 244bb and water vapor is dried, compressed and fed to a distillation train, 1234yf is recovered and unreacted 244bb is recycled to dehydrochlorination reactor. Preferably, a portion of the unreacted 244bb is recycled to the liquid phase reactor in order to purge 1233xf.

A detailed description of one preferred embodiment of the integrated process of the present invention is as follows:

(1) Hydrofluorination of TCP, 1,1,2,3-tetrachloro-propene, to form 1233xf using a single reactor or a multistage reactor or a series of reactors in the vapor phase containing catalyst using a combination of recycle stream(s), fresh HF and fresh TCP as illustrated in the FIGURE (at Scheme 1) as "R-1, Step 1 Reactor". In the preferred embodiment, the reaction is carried out under conditions effective to provide at least 50% conversion, preferably 80% to 85% conversion of TCP to 1233xf where the mole ratio of HF to TCP is about 20:1, reaction temperature is about 300° C. and pressure is about 120 psig.

(2) Cool the above (1) reactor effluent containing 1233xf, HCl, excess HF and any unreacted TCP plus intermediates and feed this stream into a Quench/Recycle Column for separation of unreacted TCP plus intermediates and excess HF for recycle to (1) and; 1233xf, HCl and HF to liquid phase reactor (3), as illustrated in the FIGURE (at Scheme 1) as "R-2 Step 2 Reactor".

(3) Feed the 1233xf, HCl and HF to a liquid phase reactor containing catalyst (see the catalyst choices listed above) for hydrofluorination of 1233xf to 244bb. In the preferred embodiment, the reaction is carried out under conditions effective to provide at least 96% conversion, preferably 98% conversion of 1233xf to 244bb where the mole ratio of HF to 1233xf is about 20:1, reaction temperature is about 85° C. and pressure is about 100 psig.

(4) A mixture of 244bb, HCl, unreacted 1233xf and HF exit the liquid reactor system via a catalyst stripper which is used such that most of the unreacted HF and catalyst is refluxed back to the reactor.

(5) The effluent from the catalyst stripper may be passed through a bed containing $SbCl_5$/Carbon catalyst for further conversion of 1233xf to 244bb in order to achieve a total of 98% conversion as stated in (3) above.

(6) The effluent from the catalyst stripper (4) or the effluent from $SbCl_5$/C bed (5) is fed to an HCl column to separate essentially pure HCl in the overhead from the mixture of 244bb, 1233xf, HF and HCl.

(7) The essentially pure HCl product from (6) above may be recovered as is or passed through silica gel for residual HF removal and absorbed into water.

(8) The mixture of 244bb, 1233xf, HF from (6) above is fed to an HF recovery system to separate a stream rich in organic and a stream rich in HF. Such methods include phase separation and preferential absorption of HF into sulfuric acid.

(9) The organic stream which contains minimal amount of HF is fed either directly to a dehydrochlorination reactor or further deacidified before being fed to the dehydrochlorination reactor (10) below.

(10) The 244bb stream is dehydrochlorinated using a vapor phase reactor containing dehydrochlorination catalyst. In the preferred embodiment, the reaction is carried out under conditions effective to provide at least 20% conversion, preferably at least 50% conversion of 244bb to 1234yf where the reaction temperature is about 400° C. and pressure is about 15 psig. Optionally, this stream may be dehydrochlorinated in a liquid phase reactor in the presence of an aqueous base solution such as NaOH or KOH at temperatures of about 50° C. See Scheme 2 in the FIGURE.

(11) If a vapor phase dehydrochlorination reactor is used, the effluent from (10) above containing 1234yf, HCl and unreacted 244bb is deacidified in absorption equipment (KOH or NaOH scrubbing), dried with 3A mole sieves or another suitable drying agent as disclosed herein, compressed and fed to a distillation train where 1234yf is recovered and unreacted 244bb recycled to dehydrochlorination reactor (10) above. A portion of the unreacted 244bb may be recycled to the liquid phase reactor (3) in order to purge this section of 1233xf.

(12) If a liquid phase dehydrochlorination reactor is used, the effluent from (10) above containing 1234yf, unreacted 244bb and water vapor is dried with a suitable drying agent, compressed and fed to a distillation train where 1234yf is recovered and unreacted 244bb recycled to dehydrochlorination reactor (10) above. A portion of the unreacted 244bb may be recycled to the liquid phase reactor (3) in order to purge this section of 1233xf.

(13) Drying can be done by any suitable drying method, such as for example, with sulfuric acid or a particulate desiccant. The term desiccant means any material which will absorb water without dissolving in or otherwise contaminating the fluorocarbon being dried. Such desiccants include alumina, silica gel, molecular sieves (e.g., 3A), calcium sulfate ($CaSO_4$) and $CaCl_2$, and the like

(14) In one embodiment, a packed tower is utilized and strong sulfuric acid is circulated over the column as a gaseous stream of the fluorocarbon feed material is fed to the column and the moisture in the stream is removed by reaction with the sulfuric acid.

(15) In another embodiment, the particulate desiccant is packed into a drying vessel and the liquid or gaseous fluorocarbon is passed over the material such that the moisture in the stream is removed by the desiccant.

EXAMPLE

The following non-limiting example is prospective and represents results obtained from standard process simulation and physical property prediction procedures in order to illustrate the invention. In the table below:

"R-1 Inlet" is the stream fed to the first hydrofluorination reactor.

"R-1 Exit" is the resulting effluent with reactor operating under preferred conditions.

"Quench Overhead" and "R-1 Recycle" respectively are the overhead and bottoms streams exiting a distillation tower whose primary purpose is to separate TCP and HF from the reaction products for recycle back to the first hydrofluorination reactor.

TABLE 1

R-1
Composition percentages, wt % for various streams

|  | R-1 Inlet | R-1 Exit | Quench Overhead | R-1 Recycle |
| --- | --- | --- | --- | --- |
| Temperature ° C. | 300 | 300 | 48.8 | 93.9 |
| Pressure psig | 119.73 | 119.5 | 110 | 110 |
| TCP + 1231 + 1232 | 33.9% | 5.7% | 0.0% | 10.1% |
| HF | 65.8% | 56.2% | 14.2% | 89.3% |
| HCl | 0.0% | 17.3% | 39.3% | 0.0% |
| 245cb | 0.3% | 0.8% | 1.1% | 0.6% |
| 244bb | 0.0% | 0.0% | 0.0% | 0.0% |
| 1234yf | 0.0% | 0.1% | 0.2% | 0.0% |
| 1233xf | 0.0% | 19.8% | 45.1% | 0.0% |

In the table below:

"R-2 Inlet" is the stream fed to the second hydrofluorination reactor.

"R-2 Exit" is the resulting effluent with reactor operating under preferred conditions.

"Recovered HCl" is the overhead stream from a distillation tower whose primary purpose is to separate HCl from a mixture of reactants and reaction products.

"R-2 Recycle" is the stream resulting from the HF Recovery section of the process. It is the resulting stream from subjecting the bottoms of the above distillation tower to HF recovery.

TABLE 2

R-2
Composition percentages, wt % for various streams

|  | R-2 Inlet | R-2 Exit | Recovered HCl | R-2 Recycle |
| --- | --- | --- | --- | --- |
| Temperature ° C. | 85 | 61.9 | −42.8 | 85 |
| Pressure psig | 100 | 100 | 80 |  |
| TCP + 1231 + 1232 | 0.0% | 0.0% | 0.0% | 0.0% |
| HF | 49.8% | 46.0% | 21 ppm | 93.8% |
| HCl | 21.6% | 21.7% | 99.80% | 0.0% |
| 245cb | 0.6% | 1.2% | 0.0% | 0.0% |
| 244bb | 3.0% | 30.4% | 0.19% | 6.1% |
| 1234yf | 0.1% | 0.1% | nil | 0.0% |
| 1233xf | 24.8% | 0.5% | 0.0% | 0.1% |

In the table below:

"R-3 Inlet" is the stream fed to the dehydrochlorination reactor.

"R-3 Exit" is the resulting effluent with reactor operating under preferred conditions.

"1234yf Product" is the recovered product from a purification train.

"R-3 Recycle" is a stream resulting from the purification train. In this example, this stream is recycled to the dehydrochlorination reaction. Optionally, a portion of it (or all of it) may be recycled to the second hydrofluorination reactor to reduce the 1233xf content.

TABLE 3

R-3
Composition percentages, wt % for various streams

|  | R-3 Inlet | R-3 Exit | 1234yf Product | R-3 Recycle |
| --- | --- | --- | --- | --- |
| Temperature ° C. | 400 | 400 | 27.1 | 86.9 |
| Pressure psig | 15 | 15 | 90 |  |
| TCP + 1231 + 1232 | 0.0% | 0.0% | 0.0% | 0.0% |
| HF | 0.0% | 0.1% | 0.0% | 0.0% |
| HCl | 0.0% | 3.6% | 0.0% | 0.0% |
| 245cb | 0.7% | 0.4% | 0.5% | 0.0% |
| 244bb | 73.3% | 58.2% | 0.0% | 68.9% |
| 1234yf | 0.1% | 11.5% | 99.5% | 0.0% |
| 1233xf | 25.9% | 26.3% | 0.0% | 31.1% |

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the formation of 2,3,3,3-tetrafluoro-2-propene (HFO-1234yf) from 1,1,2,3-tetrachloropropene (TCP), wherein the reaction includes the following steps:
  (a) conducting the hydrofluorination reaction of TCP with HF under conditions effective to provide at least 85%, conversion of TCP to 2-chloro-3,3,3-trifluoropropene (1233xf), where the mole ratio of HF to TCP is about 20:1, the reaction temperature is about 300° C. and the reaction pressure is about 120 psig;
  (b) cooling the effluent from step (a) which contains 1233xf, HCl, HF and any unreacted TCP, and separating any unreacted TCP for recycle to step (a);
  (c) feeding the mixture of 1233xf, HCl and HF from step (b) to a liquid phase reactor containing catalyst for hydrofluorination of the 1233xf to 2-chloro-1,1,1,2- tetrafluoropropane (244bb), under conditions effective to provide at least 98% conversion of 1233xf to 244bb, where the mole ratio of HF to 1233xf is about 20:1, the reaction temperature is about 85° C. and the reaction pressure is about 100 psig;

(d) feeding the mixture of 244bb, HCl, unreacted 1233xf and HF formed in step (c) to a catalyst stripper, from which unreacted HF and catalyst are recycled to the step (c) reactor;

(e) feeding the effluent from the catalyst stripper through a bed containing $SbCl_5$/Carbon catalyst for further conversion of 1233xf to 244bb;

(f) feeding the effluent from the $SbCl_5$/C catalyst bed in step (e) to a column to separate the HCl from the mixture of 244bb, 1233xf, HF and HCl;

(g) feeding the mixture of 244bb, 1233xf, HF from step (f) to an HF recovery system by subjecting the mixture to a phase separation to separate a stream rich in organic and a stream rich in HF;

(h) feeding the organic stream from step (g) to a dehydrochlorination reactor and dehydrochlorinating the 244bb mixture under conditions effective to provide 1234yf and unreacted 244bb and recycling unreacted 244bb to step (c).

2. The process of claim 1, wherein the dehydrochlorination is conducted using a vapor phase reactor containing catalyst, where the reaction temperature is about 400° C. and the reaction pressure is about 15 psig.

3. The process of claim 2, wherein the effluent from step (h) containing 1234yf, HCl and unreacted 244bb is deacidified, dried, compressed and distilled so that the 1234yf is recovered and unreacted 244bb is recycled to the dehydrochlorination reactor in step (h).

4. The process of claim 1, wherein the dehydrochlorination is conducted in a liquid phase reactor in the presence of an aqueous base at a temperature of about 50° C.

5. The process of claim 4, wherein the effluent from step (h) is dried, compressed and distilled, so that 1234yf is recovered and unreacted 244bb is recycled to the dehydrochlorination reactor in step (h).

6. The process of claim 4, wherein any unreacted 244bb is recycled to the liquid phase reactor in step (c).

* * * * *